United States Patent [19]
Ranby

[11] Patent Number: 5,114,845
[45] Date of Patent: May 19, 1992

[54] ASSAYS FOR PLASMINOGEN ACTIVATOR INHIBITOR AND SOLUBLE FIBRIN

[75] Inventor: Mats G. Rånby, Umea, Sweden

[73] Assignee: Biopool International, Inc., New York, N.Y.

[21] Appl. No.: 391,744

[22] Filed: Aug. 9, 1989

Related U.S. Application Data

[62] Division of Ser. No. 70,068, Jul. 6, 1987, abandoned.

[51] Int. Cl.$^5$ .............................................. C12Q 1/56
[52] U.S. Cl. ...................................... 435/13; 435/23; 530/328; 930/10; 930/240
[58] Field of Search ................... 435/13, 23, 212, 217; 930/240; 530/381, 382

[56] References Cited

U.S. PATENT DOCUMENTS

| | | |
|---|---|---|
| 4,181,690 | 4/1989 | Paques. |
| 4,534,972 | 8/1985 | Lembach. |
| 4,563,420 | 1/1986 | Verheijen et al.. |
| 4,710,459 | 12/1987 | Bartl et al. ............................ 435/13 |
| 4,780,419 | 10/1988 | Uchida et al.. |

OTHER PUBLICATIONS

Wiman et al., "Determination of Soluble Fibrin in Plasma by a Rapid and Quantitative Spectrophotometric Assay", Thrombosis and Haemestasis, 55(2), pp. 189–193 (1986).
Tate et al., "Functional Role of Proteolytic Cleavage at Arginine-275 of Human Tissue Plasminogen Activator as Assessed by Site-Directed Mutagenesis", Biochemistry 26(2), pp. 338–343 (Jan. 27, 1987).
Wiman et al., "Plasminogen Activator Release During Venous Stasis and Exercise as Determined by a New Specific Assay", Clin. Chem. Acta, vol. 127, pp. 279–288 (1983).
Allen, "An Enhancing Effect of Poly-Lysine on the Activation of Plasminogen", Thromb. Haemostas., vol. 47, No. 1, pp. 41–45 (1982).
Chmielewska et al., "Evidence for a Rapid Inhibitor to Tissue Plasminogen Activator in Plasma", Thromb. Res., vol. 31, pp. 427–436 (1983).
Haeggroth et al., "Plasminogen Activator Inhibitors in Plasma and Platelets from Patients with Recurrent Venous Thrombosis and Pregnant Women", Thromb. Res., vol. 42(5), pp. 585–594, (1986).
Eriksson et al., "Determination of Plasminogen Activator Inhibitor in Plasma Using t-PA and a Chromogenic Single-Point Poly-D-Lysine Stimulated Assay", Thromb. Res., vol. 50, pp. 91–101 (1988).
Berne et al., editor, Physiology, pp. 382–385 (1988).
L. Lorand, editor, "Proteolytic Enzymes", Methods in Enzymology, vol. 80, Pt. C, Academic Press, Inc., pp. 365–378 (1981).
Wiman et al., "The Role of the Fibrinolytic System in Deep Vein Thrombosis", J. Lab. Clin. Med., pp. 265–270 (Feb. 1985).
Ranby et al., "Age Dependence of Tissue Plasminogen Activator Concentrations, Plasma, as Studied by an Improved Enzyme-Linked Immunosorbent Assay", Clin. Chem., vol. 32, pp. 2160–2165 (1986).
Ranby et al., "A Sensitive Assay for Tissue Plaminogen Activator", Thromb. Res., vol. 27.27, pp. 743–749 (1982).
Rijken et al., "Measurement of Human Tissue-Type Plasminogen Activator by a Two-Site Immunoradiometric Assay", J. Lab. Clin. Med., vol. 101, No. 2, pp. 274–284 (1983).
Bergsdorf, "An Enzyme-Linked Immunosorbent Assay for Determination of Tissue Plasminogen Activator Applied to Patients with Thromboembolic Disease", Thromb. Haemostas., vol. 50, No. 3, pp. 740–744 (1983).
Holvoet et al., "Assay of Human Tissue-Type Plasminogen Activator with an ELISA Based on Three Murine Monoclonal Antibodies to Tissue Plasminogen Activator", Thromb. Haemostas., vol. 54, No. 3, pp. 684–687 (1985).
Faulkner, W. R., edit., "Selected Methods for Small Chemistry Laboratory", Selected Methods of Clinical Chemistry, vol. 9, pp. 6–7 and 328.

*Primary Examiner*—Esther L. Kepplinger
*Assistant Examiner*—Carol E. Bidwell
*Attorney, Agent, or Firm*—Jones, Askew & Lundsford

[57] ABSTRACT

The present invention relates to an improved method for measuring soluble fibrin utilizing a genetically modified tissue plasminogen activator protein as a substrate.

1 Claim, No Drawings

ASSAYS FOR PLASMINOGEN ACTIVATOR INHIBITOR AND SOLUBLE FIBRIN

This application is a division of application Ser. No. 070,068, filed Jul. 6, 1987 now abandoned.

TECHNICAL FIELD

The present invention relates to an improved method for measuring tissue plasminogen activator, plasminogen activator inhibitor, and soluble fibrin. More particularly, the present invention relates to a method for measuring plasminogen activator inhibitor and soluble fibrin which utilizes a genetically modified tissue plasminogen activator protein as a reagent. The present invention also relates to improved methods of collecting blood so that endogenous plasminogen activator is not inactivated.

BACKGROUND

The term "tPA" means "tissue plasminogen activator". The term "PAI" means plasminogen activator inhibitor. "PAI 1" is plasminogen activator inhibitor one and is sometimes called endothelial plasminogen activator inhibitor. "PAI 2" is plasminogen activator inhibitor two and is sometimes called placental plasminogen activator inhibitor. The term "$\alpha_2$AP" means alpha 2 antiplasmin and is a protein found in blood of normal individuals that inhibits the enzyme plasmin. The term "fibrinogen digests" includes the products from digestion of fibrinogen or fibrin with proteolytic enzymes, such as plasmin.

Investigation of tissue plasminogen activator inactivation in plasma has been hampered by poor methodology. A specific and sensitive method for measuring tPA in plasma samples where potential fibrinolytic inhibitors were neutralized by controlled acidification was described. (See Wiman, B., et al., *Clin. Chim Acta*, 127, 279–288, 1982). tPA subsequently measured by this method exhibited a parabolic rate assay. (See Rånby, M., et al, *Thromb. Res.* 27, 743–749, 1982). With this method it was also possible to specifically determine inhibitory activity to tPA in plasma and kinetic evidence for a fast tPA inhibitor in plasma was presented.

Assuming the formation of a stoichiometric 1:1 complex, a rate constant of about $10^7$ $M^{-1}\cdot s^{-1}$ was calculated, and the plasma concentration of the new inhibitor in healthy individuals was determined as $8\pm2$ unit/ml (1 unit=inhibition of 1 international unit of tPA). The tPA inhibitory content was also determined in plasma from various patients. High inhibitory activity content was frequently found in patients with deep venous thrombosis, hemostatic problems during late pregnancy, or severe coronary heart disease. (See Chmielewska, J., et al., *Thromb. Res.* 31, 427–436 (1983)). The PAI activity observed is now known to be the result of PAI1 activity.

There are several assay systems that are commercially available for the measurement of tPA and PAI which utilize native tPA. However, the results concerning PAI levels obtained from these assays are not always reliable because of the cleavage of tPA into the two chain form of the protein. Native one-chain tPA is cleaved by plasmin or by trypsin after the Arg in the sequence -Gln-Phe-Arg-Ile-Lys- in the tPA protein. This creates a problem when trying to measure the PAI1 level in a biological fluid by inhibition of the tPA activity because two chain tPA also reacts rapidly with PAI 2 and reacts much faster than single chain tPA with other protease inhibitors such as $\alpha_2$AP.

Thus, what is needed is a tPA that is resistant to cleavage by proteolytic enzymes to prevent formation of two chain tPA in the preparation procedure or during the assay procedure. With such a tPA, levels of PAI1 activity could be more accurately measured.

Another problem encountered in the prior art methods of measuring tPA and PAI is the fact that tPA and PAI1 activity are unstable after blood is collected and the activity of the two proteins decreases after blood is collected. In blood with high PAI1 levels, the tPA activity can decrease by 50% in about one minute. The PAI1 activity typically has a half life of 4 hours at room temperature.

When tPA is assayed in blood, it has been found that polylysine is an effective stimulator of tPA activity. However, it has also been found that polylysine is not an effective activator of tPA in biological fluids other than blood and blood plasma. Thus, what is needed is to identify the preparation in plasma that, together with polylysine, constitutes the effective tPA stimulator which will allow one to design better methods to determine the tPA level. The improved methods will allow one to perform tPA activity assays in non-plasma systems.

Another problem encountered in the prior art is that plasma samples must be acidified and incubated for relatively long periods of time at low pH to destroy the plasmin inhibitory activity in the plasma sample that interferes with the assay. What is needed is to identify the inhibitory activity and neutralize this with specific antibodies. This will make both tPA activity and PAI activity more convenient to assay.

Yet another problem encountered in the prior art of determining tPA activity is that the tPA activity is underestimated in biological fluids that also contain PAI1 activity. This is because PAI1 in this study is found to be relatively stable during acidification and will react with tPA when the sample is neutralized during the tPA assay procedure. What is needed is a method of inhibiting PAI1 activity in the assay system when measuring tPA activity in biological fluids.

SUMMARY OF THE INVENTION

In accordance with the present invention, variants of one-chain tPA where the -Arg- amino acid was replaced by a His (Arg to His) or by a Lys (Arg to Lys) or by a Thr (Arg to Thr) were made through genetic modification of the native tPA protein. All the mutants, including the uncleavable Arg to Thr mutant could be used in determination of PAI activity in plasma samples. The Arg to Thr mutant represents an advantage in PAI1 activity determination. Preparations of the Arg to Thr mutant are sure to be free of two chain tPA. The two chain tPA, in contrast to single chain tPA, reacts readily also with PAI 2. Thus, by using the mutant tPA one can accurately measure PAI1, an inhibitor that selectively reacts with single chain tPA. One can measure PAI1 in samples containing both PAI1 and PAI 2, e.g., plasma from pregnant women.

In addition, the present invention encompasses an improved method of collecting blood so that the tPA present in the blood is stabilized and is not readily inactivated by PAI present in the blood. The improved method of collecting blood comprises acidifying the blood from the physiological pH of about 7.3 to a pH of between approximately 4.0 to 6.0. The preferred method of acidifying the blood for assaying tPA is with citrate buffer although it is to be understood that other buffers can be used in practicing the present invention. Buffer substances that also chelate calcium ions (e.g., citrate and EDTA) are particularly suited since these buffer substances also inhibit blood coagulation. To reduce hemolysis of blood during the acidification, it has been found advantageous to add Pluronic ® F-68 to the blood citrate buffer mixture.

Another aspect of the present invention is the discovery that fibrinogen is the plasma component that together with polylysine is the stimulator of tPA. Plasmin digests of fibrinogen or fibrin will also function in this respect. Thus, when tPA is being measured in biological fluids other than blood, fibrinogen (or fibrinogen digestion products) must be added along with polylysine to obtain maximum stimulation of tPA activity.

Yet another aspect of the present invention is the verification that $\alpha_2 AP$ and PAI1 activites will interfere with assay of tPA activity. Furthermore it was found that antibodies that inhibit these activites also improve the performance of the tPA activity assay.

Accordingly, it is an object of the present invention to provide an improved method of assaying plasminogen activator inhibitor activity.

It is an object of the present invention to provide a tPA that is resistant to cleavage by proteolytic enzymes and is useful in the assay of PAI1.

It is another object of the present invention to provide a method of collecting blood or other biological fluid that will stabilize tPA activity.

Another object of the present invention is to provide a method of immediately lowering the pH of the blood with a minimum of hemolysis.

It is yet another object of the present invention to provide a method of using polylysine in combination with fibrinogen or fibrinogen digests as a tPA cofactor.

Yet another object of the present invention is to provide an improved method of measuring fibrin in a sample utilizing a single chain tPA that is resistant to cleavage by proteolytic enzymes.

Another object of the present invention is to improve the assay of tPA activity by including antibodies that inhibit PAI1 and $\alpha_2$ antiplasmin activities since these activities interfere with the assay of tPA activity.

These and other objects, features and advantages of the present invention will become apparent after a review of the following detailed description of the disclosed embodiment and the appended claims.

DETAILED DESCRIPTION OF THE DISCLOSED EMBODIMENT

Native one-chain tPA is cleaved by plasmin or by trypsin after the Arg in the sequence -Gln-Phe-Arg-Ile-Lys- in the tPA protein. This creates a problem when trying to measure the PAI level in a biological fluid by inhibition of the tPA activity. For example, tPA activity is known to be stimulated by fibrin or fibrin fragments. The stimulation of single chain tPA by the presence of fibrin is much greater than that of the two chain tPA.

The mutant tPAs in which the arginine residue in the sequence: -Gln-Pro-Gln-Phe-Arg-Ile-Lys-Gly-Gly- had been replaced were enzymatically characterized. The specific activity expressed in IU/µg were as follows: 810 (Arg to His), 640 (Arg to Lys), 290 (Arg to Thr) as compared to 810 for the wild type and 660 for Bowes melanoma tPA. The amidolytic activity against D-Ile-Pro-Arg-pNA at 37° C., pH 9.0 expressed in mOD per minute at 1 µg/ml of enzyme was 15.8 (Arg to His), 13.6 (Arg to Lys), 8.3 (Arg to Thr), 10.0 (wild type), and 9.6 for melanoma one chain tPA as compared to 55.2 for two chain melanoma tPA. Only the arginine to threonine mutant was resistant to plasmin and trypsin cleavage.

All mutant tPAs, including the uncleavable Arginine to Threonine mutant, could be used in determination of PAI activity in plasma samples. The Arg to Thr mutant represents a advantage in PAI1 activity determination. Preparations of the Arg to Thr mutant are sure to be free of two chain tPA which, in contrast to the single chain tPA, also reacts readily with PAI 2.

It is to be understood that the genetically modified tPA that is described herein are readily made by those of ordinary skill in the recombinant DNA art. In addition, it is also possible to chemically modify the tPA molecule so that the molecule is more suitable for use in the aforementioned assays. For example, the chemical modification can be performed so that the single chain tPA can no longer be cleaved by proteolytic enzymes.

The plasminogen activation rate in the presence and absence of fibrin at 0.5 µm plasminogen and 37° C. was measured and the stimulation factor calculated. This was about 950 fold for the Arg to Thr mutant which was considerably higher than that of melanoma one chain tPA and the other mutant tPA which were all about 550 fold. The stimulation factor for melanoma two chain tPA was about 120 fold. It is to be understood that the extra fibrin sensitivity of the Arg to Thr mutant resulted in an improved soluble fibrin assay according to the Wiman-Rånby protocol (See Wiman, B and Rånby, M, *Thromb. Haemostas.* 55, 189–183 (1986)). Thus, the plasmin insensitive protein-engineered mutant tPA is shown to be advantageous over prior art methods when used in assays for PAI1 activity and soluble fibrin.

It is to be understood that the tPA activity measured according to the present invention can optionally be determined using a reagent containing antibodies that inhibit anti-plasmin activity and PAI1 activity present in the biological fluid to be analyzed.

The present invention also includes a method for determining the content of soluble fibrin in a sample comprising the steps of mixing a fixed amount of sample with a fixed amount of reagent containing one-chain tPA, plasminogen and a plasmin substrate, measuring plasmin substrate cleavage and correlating this rate with the amount of soluble fibrin in the sample.

It was found that if during blood sample collecting, the pH of the blood is immediately lowered from the physiological pH 7.3 to a pH of between approximately 4.0 and 6.0, several advantages for the stability of the fibrinolytic components could be gained without introducing any disadvantages or inconveniences when compared to commonly used Vacutainer ®, Venaject ® systems for collecting blood.

According to the present invention, nine parts of blood are drawn into a container that contains one part citrate buffer with a pH of about 4 and a molarity of about 1 mol/l of citrate. The final pH of the blood sample should preferably be between approximately 4.5 to 6.5. The citrate buffer should preferably be between 0.5 to 2 mol/l of a sodium citrate buffer at a pH of approximately 4.0 to 5.5 to which 5 to 15 parts by volume of blood are added during collection.

To prevent hemolysis of the red blood cells and thrombocyte activation in the blood sample, Pluronic® F-68 (BASF Corporation, Parsippany, N.J.) can optionally be included in the solution into which the blood is being collected. The optimal final concentration of Pluronic® F-68 is between approximately 0.01% to 0.1% (0.1 to 1 mg/ml). It is to be understood that other Pluronic® surfactants can be used in the present invention to prevent hemolysis.

The Pluronic® F-68 is a species within the following general formula:

wherein a is an integer such that the hydrophobe represented by ($C_3H_6O$) has a molecular weight of approximately 950 to 4000, preferably about 1750 to 3500, and b is an integer such that the hydrophile portion represented by ($C_2H_4O$) constitutes approximately 50% to 90% by weight of the compound.

Pluronic® F-68 has the following specific formula:

wherein the molecular weight of the hydrophobe ($C_3H_6O$) is approximately 1750 and the total molecular weight of the compound is approximately 8400.

The advantages of the procedure are that the rates of the reactions between tPA and PAI1 and between tPA and other inhibitors of blood are reduced at a pH of about 5 as compared to those at the physiological pH of about 7.3. These reduced reaction rates will greatly increase the stability of tPA activity in plasma. This is most important since it is relevant to determine the tPA activity at the time of sampling and not the lower tPA activity found in stored blood samples collected according to the prior art. Thus, the present invention will improve the value of measuring tPA activity to diagnose the etiology of thrombotic disease, the risk of developing thrombotic disease, or the tPA activity obtained during tPA therapy.

It has been determined that the stability of PAI1 activity is increased significantly in blood samples collected according to the present invention as compared to those collected in a conventional way. This is of importance for this type of assay since the instability of PAI1 activity is limiting the spread of this clinically important assay.

In addition, the method according to the present invention preserves soluble fibrin levels in blood and plasma samples thereby improving the diagnostic importance of this important assay. High levels of soluble fibrin are found in the blood of patients with malignancies, risk pregnancies and in patients suffering from severe trauma. High levels of soluble fibrin is also a symptom of disseminated intravascular coagulation.

The present invention is advantageous when monitoring fibrinogen and FVII levels during tPA therapy. This is because plasmin generation is slow at the lower pH thereby eliminating much of the artifacts caused in vitro by the action of in vitro generated plasmin.

Thus, the present invention of lowering the pH of blood during collection greatly improves the stability in the blood sample and in the plasma sample derived thereof of several important fibrinolytic parameters namely tPA activity, PAI1 activity and soluble fibrin as well as fibrinogen and other coagulation factors such as FVIII and FV.

It has been determined that in the use of poly-D-lysine stimulation for tPA mediated plasminogen activation, it was found the human plasma contained a factor which increased the stimulating effect of poly-D-lysine. In this work, this factor was identified as fibrinogen and it was further found that the plasmin digestion products of fibrinogen or fibrin also had the effect. This discovery is important because it makes possible the formulation of practical and inexpensive reagents for determining tPA activity in blood plasma and PAI1 activity in blood plasma. This is most important in the clinical routine.

EXAMPLE I

The following example describes measurement of tPA according to the present invention:

Citric acid monohydrate, $M_r=210$, and Tri-sodium citrate dihydrate, $M_r=294$, is obtained from Merck Darnstadt, W. G. Pluronic® F-68 is obtained from BASF Corporation, Parsipanny, N.J. Blood is obtained by vein puncture and collected on 0.13 mol/l trisodium citrate (1 part citrate buffer to 9 parts blood) in a siliconized Venoject® collection tube.

0.5 mol/l solutions of citric acid and of tri-sodium citrate are mixed to give 0.5 mol/l sodium citrate solutions with pH of 4.0, 4.5, 5.0 and 5.5. Each of these solutions is aliquoted and 25% F68 is added to give final concentrations of 0, 0.1 or 1% by weight.

1.0 mol/l and 2.0 mol/l citrate buffers pH 4.0, 4.5, 5.0 and 5.5 containing 0, 0.1 or 1% F68 are made accordingly.

Citrated blood is dispensed in 300 μl aliquoted to which 33 μl of each of the 36 different buffers are added, mixed and incubated at room temperature (22° C.) for 20 hours. The samples are centrifuged six minutes at 1500×g, diluted six fold in 0.15 mol/l NaCl and subjected to pH and absorptivity at 537 nm determination. The absorption value (optical density at 1 cm path length) is multiplied by the dilution factor of 6.

Thus, to a series of blood sample aliquots 1:9 volume of various citrate buffers are added. Plasma is obtained some 20 hours later and the pH and 537 nm absorptivity is determined. The results are shown in Table 1.

TABLE 1 pH and absorption at 537 nm for plasma obtained from blood samples to which 1:9 volume of citrate buffers with various concentrations, pH and F68 content are added.

| | 0.5 mol/l Citrate Conc. F68 (mg/ml) | | | 1.0 mol/l Citrate Conc. F68 (mg/ml) | | | 2.0 mol/l Citrate Conc. F68 (mg/ml) | | |
|---|---|---|---|---|---|---|---|---|---|
| pH | 0 | 1 | 10 | 0 | 1 | 10 | 0 | 1 | 10 |
| 4.0 pH | 5.62 | 5.50 | 5.58 | 4.88 | 4.90 | 4.94 | 4.62 | 4.58 | 4.60 |
| A | 0.54 | 0.51 | 0.75 | 4.61 | 3.32 | 2.24 | 10.92 | 10.5 | 11.6 |
| 4.5 pH | 6.07 | 6.04 | 6.09 | 5.48 | 5.44 | 5.41 | 5.08 | 5.10 | 5.10 |
| A | 0.62 | 0.56 | 0.55 | 0.61 | 0.49 | 0.46 | 5.24 | 1.09 | 1.40 |
| 5.0 pH | 6.50 | 6.48 | 6.52 | 5.92 | 5.83 | 5.90 | 5.58 | 5.51 | 5.53 |
| A | 0.67 | 0.73 | 0.678 | 0.53 | 0.48 | 0.44 | 0.92 | 0.92 | 0.91 |
| 5.5 pH | 6.78 | 6.83 | 6.92 | 6.34 | 6.33 | 6.35 | 6.02 | 5.93 | 5.99 |
| A | 0.72 | 0.68 | 0.65 | 0.84 | 0.70 | —* | 0.51 | 1.10 | 1.29 |

*not determined

As can be seen from Table 1, the addition of F68 to the freshly collected blood reduced the disruption of the red blood cells as indicated by the absorbance at 537 nm. This is particularly clear with the addition of 1 mol/l citrate at a pH of 4.0 and with the addition of 2 mol/l citrate at a pH of 4.5. In both cases, there is a dose dependent increase in the stability of the red blood cell membranes as shown by absorbance at 537 nm decreases as the Pluronic ® F-68 concentration increases. It should be noted that this experiment is performed with blood of an apparently healthy individual and problems with hemolysis are small. These problems can be expected to be much greater when large numbers of patient plasmas are sampled.

EXAMPLE 2

Venoject ®, Terumo Europe, Lewen, Belgium, are evacuated siliconized 4.5 ml of tubes containing 0.45 ml 0.13 mol/l sodium citrate and are, in the following, called "Venoject regular". Some "Venoject regular" aer modified as an embodiment of the present invention. The citrate buffer in the "Venoject regular" tubes is removed by suction with a hypodermic needle and 0.45 ml 1.0 mol/l citrate buffer pH 4.0 is introduced through the rubber stopper with a hypodermic needle. In this way, the citrate buffer content is changed without disturbing the vacuum in the tube. The modified tubes are hereinafter called "Venoject modified".

Blood is drawn by vein puncture from an apparently healthy individual into two "Venoject regular" and into two "Venoject modified" tubes. To one "Venoject regular" and one "Venoject modified" tube, 45 µl of 500 IU/ml single chain tPA dissolved in 1.0 mol/l KHCO$_3$ is added. This results in an increase in tPA activity by about 8.9 IU/ml in the plasma (haematocrit of 0.45). The four tubes, "Venoject regular", "Venoject regular+tPA", "Venoject modified" and "Venoject modified+tPA" are incubated at room temperature (22° C.) and 1 ml aliquots are drawn after 0.25, 1, 2 and 3 hours. The aliquots are centrifuged six minutes at 1500×g and 100 µl plasma is acidified by addition of 100 µl mol/l acetate buffer pH 3.9 and analyzed according to the protocol of Wiman, et al. *Clin. Chem. Act.* 127:279-288 (1983) using Spectrolyse/fibrin reagents from Biopool AB, Umeå, Sweden. The results of the study are shown in Table 2.

In Table 2, tPA activity in blood plasma is measured after blood sample collection in "Venoject regular" and "Venoject modified" with and without addition tPA. The blood is incubated at room temperature for 0.25, 1, 2 and 3 hours before separation of the blood cells. tPA activity found in the plasma is expressed in IU/ml.

TABLE 2

| Time Hours | Venoject Regular | Venoject Regular and tPA | Venoject Modified | Venoject Modified and tPA |
|---|---|---|---|---|
| 0.25 | 0.51 | 3.8 | 1.3 | 8.4 |
| 1 | 0.14 | 1.7 | 1.6 | 9.6 |
| 2 | 0.07 | 0.6 | 1.4 | 9.6 |
| 3 | 0.04 | 0.4 | 1.4 | 9.9 |

As seen in Table 2, tPA is stable in Venoject modified tubes while tPA activity in unmodified tubes decreased rapidly.

It should be understood that the foregoing relates only to a preferred embodiment of the present invention and that numerous modifications or alterations may be made without departing from the spirit and scope of the invention as set forth in the appended claims.

I claim:

1. A method for determining the amount of soluble fibrin in a sample comprising the steps of:
    a. mixing a fixed amount of sample with a fixed amount of reagent containing single chain tPA, wherein the arginine residue in the sequence -Gln-Pro-Gln-Phe-Arg-Ile-Lys-Gly-Gly of the tPA has been substituted with a threonine, plasminogen and a plasmin substrate;
    b. measuring the rate of plasmin substrate cleavage;
    c. correlating this with the amount of soluble fibrin in the sample.

* * * * *